United States Patent [19]

Andrieu et al.

[11] Patent Number: 5,589,190
[45] Date of Patent: Dec. 31, 1996

[54] SUSTAINED-RELEASE COMPOSITIONS OF ALFUZOSIN HYDROCHLORIDE

[75] Inventors: Véronique Andrieu, Boulogne Billancourt; Jean Montel, Chatou; Alexander Wick, Saint Nom La Bretèche, all of France

[73] Assignee: Synthelabo, Le Plessis Robinson, France

[21] Appl. No.: 406,405

[22] Filed: Mar. 20, 1995

[30] Foreign Application Priority Data

Mar. 21, 1994 [FR] France ................... 94 03257

[51] Int. Cl.⁶ .................. A61K 31/505; A61K 9/24; A61K 9/32; A61K 9/58
[52] U.S. Cl. .................. 424/462; 424/474; 424/482; 424/487; 424/497; 514/260
[58] Field of Search ............ 514/260; 424/474, 424/482, 487, 497, 462

[56] References Cited

U.S. PATENT DOCUMENTS

| | | | |
|---|---|---|---|
| 4,315,007 | 2/1982 | Manovry | 424/251 |
| 4,661,491 | 4/1987 | Regnier | 514/200 |
| 4,713,248 | 12/1987 | Kjornaes et al. | 424/468 |
| 4,716,041 | 12/1987 | Kjornaes et al. | 424/488 |
| 4,925,837 | 5/1990 | Cavero et al. | 514/211 |
| 5,169,642 | 12/1992 | Brinker et al. | 424/488 |
| 5,175,003 | 12/1992 | Goldman | 424/484 |
| 5,202,128 | 4/1993 | Morella et al. | 424/269 |
| 5,229,131 | 7/1993 | Amidon et al. | 424/451 |
| 5,268,182 | 12/1993 | Brinker et al. | 424/488 |
| 5,316,772 | 5/1994 | Jurgens et al. | 424/472 |
| 5,316,774 | 5/1994 | Evry et al. | 424/501 |
| 5,330,766 | 7/1994 | Morrella et al. | 424/490 |
| 5,445,828 | 8/1995 | Pozzi et al. | 424/476 |
| 5,472,710 | 12/1995 | Klokkers-Bethke et al. | 424/468 |

OTHER PUBLICATIONS

Abstract of: Illum WO/PCT 94/27582 (94/12/08) (Priority G.B. May 29, 1993—93–11191).
Hieble WO/PCT 93/19758 (93/10/14).
Gormley WO/PCT 92/16213 (93/10/01).
Cavero EP 189 336 (86/07/30).

*Primary Examiner*—Shep K. Rose
*Attorney, Agent, or Firm*—Foley & Lardner

[57] ABSTRACT

Pharmaceutical compositions which comprises a core comprising alfuzosin hydrochloride which core is coated with a coating whose dissolution is pH-dependent and applications to the preparation of sustained-release dosage compositions which are unable for a once-daily oral administration.

14 Claims, 1 Drawing Sheet

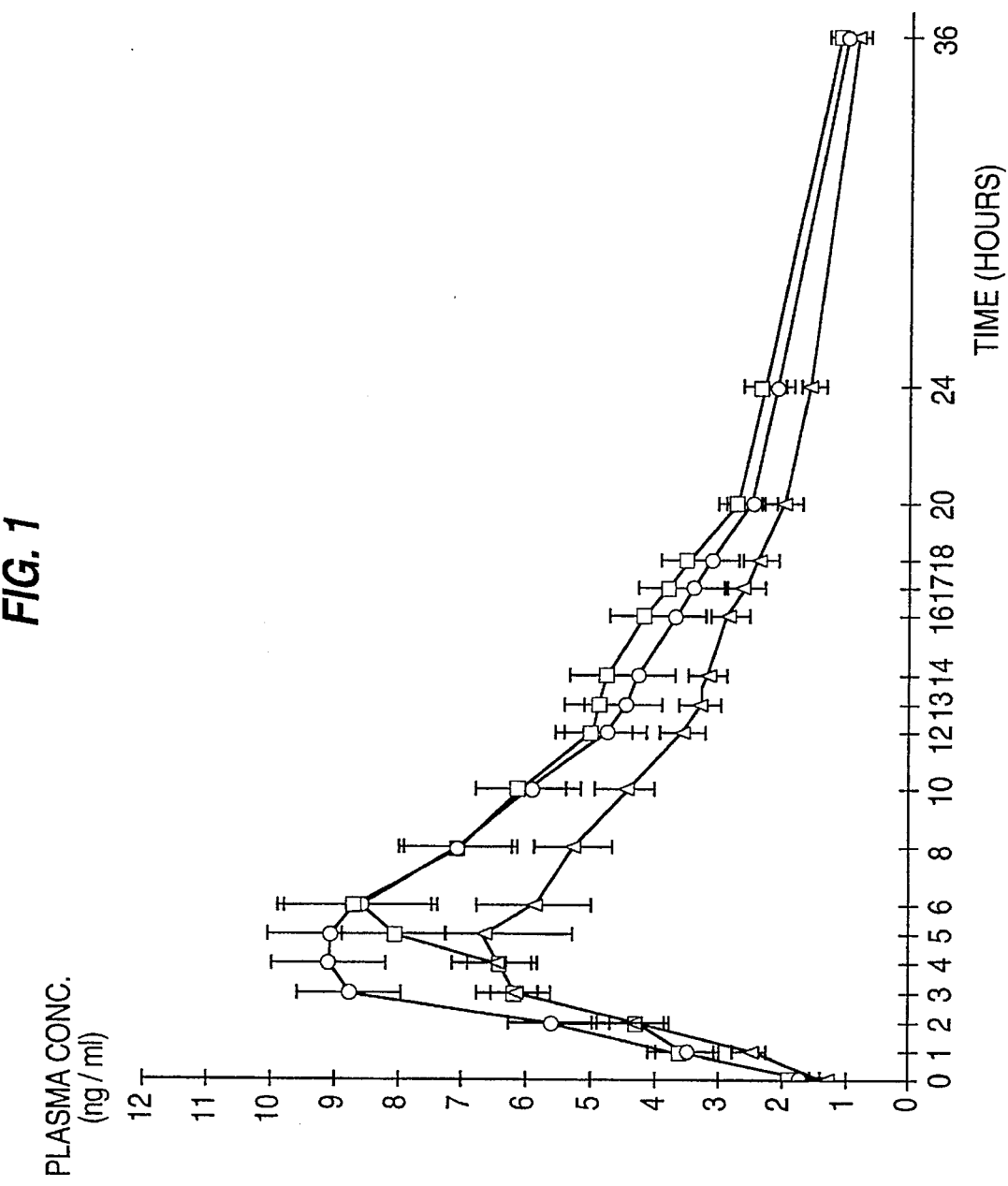

SUSTAINED-RELEASE COMPOSITIONS OF ALFUZOSIN HYDROCHLORIDE

The present invention relates to targeted-release pharmaceutical forms of alfuzosin hydrochloride and to their application to the preparation of sustained-release dosage forms which are usable for a once-daily administration.

Alfuzosin hydrochloride, used orally in the symptomatic treatment of benign prostatic hypertrophy, displays an absorption whose intensity decreases along the digestive tract, absorption being low in the ileum and colon.

According to a traditional oral form, this compound must hence be administered several times daily.

For alfuzosin hydrochloride, a sustained-release oral form enabling a constant plasma concentration which is sufficient over 24 hours to be obtained must effect its release and its absorption mainly in the lower portions of the digestive tract.

The new dosage forms according to the present invention enable the release of alfuzosin hydrochloride in the digestive tract to be targeted, and are applicable to a once-daily oral administration while being very safe as regards any excessively rapid release.

The pharmaceutical forms (compositions) according to the invention contain a core, namely a tablet affording immediate release or sustained release or microparticles affording immediate release of alfuzosin hydrochloride, coated with a membrane whose nature and thickness enable the release of the active principle to be controlled on the basis of pH and time.

The tablets affording immediate or sustained release of the active principle, all the dimensions of which are less than 10 mm, contain 3 to 10% by weight of alfuzosin hydrochloride.

The first kind of tablet is prepared by aqueous granulation from the active principle and excipients such as lactose, microcrystalline cellulose, polyvinylpyrrolidone, sodium carboxymethylstarch and magnesium stearate, the second kind is prepared by aqueous granulation or melting, by combining the active principle with a lipid matrix composed, for example, of microcrystalline cellulose, dicalcium phosphate dihydrate, hydrogenated castor oil, polyvinylpyrrolidone and magnesium stearate.

The microparticles affording immediate release of the active principle contain 3 to 15% by weight of alfuzosin hydrochloride and are between 0.50 and 1.25 mm in size. They are generally prepared by aqueous granulation from the active principle, mannitol and polyvinylpyrrolidone.

The tablets and the microparticles are then surrounded by a coating film by spraying with a coating solution in an air-fluidized bed apparatus or any other satisfactory device. The coating contains a polymer whose dissolution is pH-dependent, for example Eudragit S® (methacrylic acid copolymer) which enables a coating film that dissolves at a pH above 7 to be obtained, thereby effecting a colonic release of the active principle.

The thickness of the coating film enables the latency time of release of the active principle at pH 7 to be modulated.

In the case of microparticles, the coating may further contain an impermeable polymer and be composed for example, of a combination of Eudragit S® and ethylcellulose, enabling the rate of release of the active principle to be modulated and effecting, as in the above case, a release of the active principle which is pH- and time-dependent as a result of the presence of the polymer which is soluble at a certain pH and of the thickness of the coating film.

The pharmaceutical forms according to the invention typically contain from 3 to 20 mg of alfuzosin hydrochloride.

They may be used for the preparation of sustained-release dosage forms of alfuzosin hydrochloride for a single daily administration. These dosage forms comprise one or more pharmaceutical forms having coated cores as are defined above, and possibly, one or more other pharmaceutical forms having coated or uncoated cores.

Mixing of these different forms enables the release of the active principle to be modulated over the whole length of the digestive tract.

The examples which follow illustrate the invention:

EXAMPLE 1 tablets for colonic targeting.

|  | % (by weight) |
|---|---|
| tablets |  |
| alfuzosin hydrochloride | 3.3 |
| lactose | 69.4 |
| microcrystalline cellulose | 17.8 |
| polyvinylpyrrolidone | 5.0 |
| sodium carboxymethylstarch | 4.0 |
| magnesium stearate | 0.5 |
| coating |  |
| methacrylic acid copolymer | 75.7 |
| diacetylated monoglycerides | 7.5 |
| talc | 16.8 |

EXAMPLE 2 microparticles for colonic targeting.

|  | % (by weight) |
|---|---|
| microparticles |  |
| alfuzosin hydrochloride | 7.0 |
| mannitol | 32.0 |
| microcrystalline cellulose | 56.0 |
| polyvinylpyrrolidone | 5.0 |
| coating |  |
| methacrylic acid copolymer | 65.0 |
| ethylcellulose | 35.0 |
| diacetylated monoglycerides | 9.0 |

EXAMPLE 3 tablets in a hard gelatin capsule for a once-daily oral administration.

|  | % (by weight) |
|---|---|
| tablet no. 1 |  |
| alfuzosin hydrochloride | 3.3 |
| microcrystalline cellulose | 30.0 |
| dicalcium phosphate dihydrate | 42.7 |
| hydrogenated castor oil | 18.0 |
| polyvinylpyrrolidone | 5.0 |
| magnesium stearate | 1.0 |
| tablet no. 2 |  |
| alfuzosin hydrochloride | 3.3 |
| lactose | 69.4 |
| microcrystalline cellulose | 17.8 |
| polyvinylpyrrolidone | 5.0 |
| sodium carboxymethylstarch | 4.0 |
| magnesium stearate | 0.5 |

-continued

|  | % (by weight) |
| --- | --- |
| coating of the tablet no. 2 |  |
| methacrylic acid copolymer | 75.7 |
| diacetylated monoglycerides | 7.5 |
| talc | 16.8 |

Tests of dissolution of these different pharmaceutical forms were carried out at pH 2 and at pH 7. The following results were obtained:
Formulation according Example 1, the coating representing 11% of the weight of the tablet and having a thickness of 100 μm.

|  | % dissolved | | | |
| --- | --- | --- | --- | --- |
| time (h) | 0.5 | 1.0 | 2.0 | 3.0 |
| pH 2 | 0 | 0 | 0 | 0 |
| pH 7 | 0 | 0 | 30 | 100 |

This formulation, for which the release of alfuzosin hydrochloride is zero at acid pH and complete in the space of 3 hours at pH 7, with a latency time of 1 hour, enables release of the active principle to be effected in the colon.

By varying the thickness of the coating film, it is possible to modulate the latency time of release of the active principle at pH 7.
Formulation according to Example 2, the coating representing 14% of the weight of the microparticles.

|  | % dissolved | | | | | | |
| --- | --- | --- | --- | --- | --- | --- | --- |
| time (h) | 0.5 | 1 | 2 | 3 | 4 | 6 | 8 |
| pH 2 | 0.6 | 2 | 7 | 12 | 17 | 26 | 35 |
| pH 7 | 1 | 5 | 23 | 47 | 64 | 83 | 91 |

This formulation, for which the release of alfuzosin hydrochloride varies with the pH, makes it possible to effect a rate of release of the active principle which varies over the whole length of the digestive tract.
Formulation according to Example, the coating of the tablet no. 2 representing 11% of the weight of this tablet.

|  | % dissolved | | | | | | |
| --- | --- | --- | --- | --- | --- | --- | --- |
| time (h) | 0.5 | 1 | 2 | 3 | 4 | 6 | 8 |
| pH 2 | 4 | 8 | 13 | 17 | 19 | 22 | 24 |
| pH 7 | 0.4 | 4 | 11 | 64 | 89 | 94 | 98 |

This formulation, which combines two types of tablet in the same hard gelatin capsule, effects a release of alfuzosin hydrochloride which is variable with the pH, and hence a rate of release of the active principle which is variable over the whole length of the digestive tract.

By increasing the number of tablets affording colonic targeting in the hard gelatin capsule, the amount of active principle released in the colon is increased.

The plasma kinetics of pharmaceutical forms according to the invention were also studied.

The plasma kinetics of tablets affording colonic targeting according to the formulation of Example 1 were determined in twelve healthy volunteers after a single oral administration.

The results obtained showed that the tablet of alfuzosin hydrochloride arrives in the colon after 5 hours on average, and that the active principle is released in a maximum time of 11 hours. The apparent half-life of this formulation is 9 hours.

Moreover, the plasma kinetics of hard gelatin capsules containing tablets of alfuzosin hydrochloride according to the formulation of Example 3 were studied.

BRIEF DESCRIPTION OF THE DRAWINGS

The results obtained with three types of capsule containing different proportions of the two types of tablet are shown in FIG. 1.

The curve represented by —□— represents the plasma kinetics of a hard gelatin capsule containing 1 uncoated no. 1 tablet containing 3 mg of alfuzosin hydrochloride and 3 coated no. 2 tablets each containing 3 mg of alfuzosin hydrochloride.

The curve represented by —○— represents the plasma kinetics of a hard gelatin capsule containing 1 uncoated no. 1 tablet containing 5 mg of alfuzosin hydrochloride and 2 coated no. 2 tablets having a dosage identical to that of the no. 2 tablets of the preceding case.

The curve represented by —△— represents the plasma kinetics of a hard gelatin capsule containing 1 uncoated no. 1 tablet containing 3 mg of alfuzosin hydrochloride and 2 coated no. 2 tablets having a dosage identical to that of the no. 2 tablets of the preceding cases.

The results show that this formulation, which enables the release of alfuzosin hydrochloride to be modulated over the entire length of the digestive tract, and thus the plasma kinetics to be modified, is suitable for a once-daily administration while being, as a result of the combination of dependency on time and on pH, very safe for avoiding any more rapid release.

We claim:

1. Dosage composition which comprises at least one coated core that contains alfuzosin hydrochloride, which core is coated with a coating that contains a polymer that is insoluble in acid and soluble at pH 7 or above, and at least one uncoated core containing alfuzosin hydrochloride.

2. Dosage composition according to claim 1, wherein the cores are contained in a hard gelatin capsule.

3. Dosage composition according to claim 1, wherein the polymer is a copolymer of methacrylic acid and methacrylic acid ester.

4. Dosage composition according to claim 1, wherein the core is a tablet or microparticles containing alfuzosin hydrochloride and excipients.

5. Dosage composition according to claim 1, wherein the core is a tablet consisting of a matrix that contains alfuzosin hydrochloride.

6. Dosage composition according to claim 1, wherein the core is microparticles and the coating is a mixture of the polymer with ethylcellulose.

7. Dosage composition according to claim 1, which contains from 3 to 20 mg of alfuzosin hydrochloride.

8. Dosage composition according to claim 1, wherein the thickness of the polymer coating targets release to the colon.

9. Dosage composition which comprises at least one coated core that contains alfuzosin hydrochloride as the only active ingredient, which core is coated with a coating containing a polymer that is insoluble in acid and soluble at pH 7 or above, and at least one uncoated core that contains alfuzosin hydrochloride.

10. A method for the treatment of the human or animal body comprising administering a dosage composition as claimed in claim 1.

11. A method for the treatment of the human or animal body comprising administering a dosage composition as claimed in claim 5.

12. A method for the treatment of a patient exhibiting symptoms of benign prostatic hypertrophy, comprising administering to a patient in need of such treatment, a dosage composition as claimed in claim 1.

13. A method for the treatment of a patient exhibiting symptoms of benign prostatic hypertrophy, comprising administering to a patient in need of such treatment, a dosage composition as claimed in claim 5.

14. A method for the treatment of a patient exhibiting symptoms of benign prostatic hypertrophy, comprising administering to a patient in need of such treatment, a dosage composition as claimed in claim 8.

* * * * *